United States Patent
Zhu et al.

(10) Patent No.: US 10,227,272 B2
(45) Date of Patent: Mar. 12, 2019

(54) PROCESSES AND APPARATUSES FOR RECOVERY OF ETHYLENE FROM HYDROCARBONS

(71) Applicant: UOP LLC, Des Plaines, IL (US)

(72) Inventors: Xin X. Zhu, Long Grove, IL (US); Joseph A. Montalbano, Elmhurst, IL (US)

(73) Assignee: UOP LLC, Des Plaines, IL (US)

(*) Notice: Subject to any disclaimer, the term of this patent is extended or adjusted under 35 U.S.C. 154(b) by 0 days.

(21) Appl. No.: 15/798,316

(22) Filed: Oct. 30, 2017

(65) Prior Publication Data
US 2018/0044265 A1 Feb. 15, 2018

Related U.S. Application Data

(63) Continuation of application No. PCT/US2016/035427, filed on Jun. 2, 2016.
(Continued)

(51) Int. Cl.
*C07C 7/00* (2006.01)
*C07C 7/04* (2006.01)
(Continued)

(52) U.S. Cl.
CPC ............ *C07C 7/005* (2013.01); *B01D 53/047* (2013.01); *B01D 53/0438* (2013.01); *C07C 7/04* (2013.01); *C07C 7/12* (2013.01); *B01D 2253/106* (2013.01); *B01D 2256/24* (2013.01); *B01D 2257/7025* (2013.01); *Y02C 20/20* (2013.01); *Y02P 20/156* (2015.11); *Y02P 20/51* (2015.11)

(58) Field of Classification Search
CPC ............... C07C 7/00; C07C 7/04; C07C 7/12

USPC ............ 585/821, 823, 824, 802, 809
See application file for complete search history.

(56) References Cited

U.S. PATENT DOCUMENTS 5,245,099 A * 9/1993 Mitariten ............... C10G 55/04
585/650
5,634,354 A 6/1997 Howard et al.
(Continued)

FOREIGN PATENT DOCUMENTS

CN 203079877 U 7/2013
CN 103304358 A 9/2013
(Continued)

OTHER PUBLICATIONS

International Search Report dated Oct. 13, 2016 in International Application No. PCT/US2016/035427.

*Primary Examiner* — Thuan D Dang

(57) ABSTRACT

Embodiments of methods and apparatuses for recovery of ethylene from FCC absorber off-gas comprising a heavy cut comprising ethylene, ethane and heavier hydrocarbons and a light cut comprising hydrogen, nitrogen and methane. An exemplary method includes passing the FCC absorber off-gas to an adsorption zone containing an adsorbent selective for the adsorption of the light cut, the adsorption zone adsorbing at least a portion of the light cut and recovering an adsorption zone effluent stream comprising the heavy cut. The adsorption zone effluent is passed to a demethanizer column to provide an overhead stream comprising hydrogen, nitrogen, methane, ethylene and ethane and a net bottoms stream comprising ethylene, ethane and the heavier hydrocarbons.

13 Claims, 2 Drawing Sheets

Related U.S. Application Data

(60) Provisional application No. 62/175,600, filed on Jun. 15, 2015.

(51) Int. Cl.
  *C07C 7/12* (2006.01)
  *B01D 53/047* (2006.01)
  *B01D 53/04* (2006.01)

(56) References Cited

U.S. PATENT DOCUMENTS

| | | |
|---|---|---|
| 5,744,687 A | 4/1998 | Ramachandran et al. |
| 5,993,516 A | 11/1999 | Morris et al. |
| 6,444,869 B2 | 9/2002 | Senetar et al. |
| 6,560,989 B1 | 5/2003 | Roberts et al. |
| 2012/0302807 A1 | 11/2012 | Elseviers |

FOREIGN PATENT DOCUMENTS

| | | |
|---|---|---|
| CN | 104030875 A | 9/2014 |
| CN | 203845966 U | 9/2014 |
| WO | 2011068642 A2 | 6/2011 |
| WO | 2012166323 A2 | 12/2012 |

\* cited by examiner

PROCESSES AND APPARATUSES FOR RECOVERY OF ETHYLENE FROM HYDROCARBONS

CROSS-REFERENCE TO RELATED APPLICATIONS

This application is a Continuation of International Application No. PCT/US2016/035427 filed Jun. 2, 2016 which application claims benefit of U.S. Provisional Application No. 62/175,600 filed Jun. 15, 2015, now expired, the contents of which cited applications are hereby incorporated by reference in their entirety.

TECHNICAL FIELD

The technical field generally relates to processes and apparatuses for recovery of ethylene. More particularly, the technical field relates to processes and apparatuses for recovery of ethylene from FCC absorber off-gas.

BACKGROUND

In a typical Fluid Catalytic Cracking (FCC) refinery, the FCC absorber off-gases contributes to approximately one-third of the refinery fuel gas production. The absorber off-gases typically contain 15 to 20 mol % ethylene and ethane. These components are valuable products. Mixtures of ethylene and ethane can be good feed sources for ethane cracking facility for ethylene production. Currently most ethylene and ethane in FCC off-gas is burned instead of recovered. Removal of ethylene and heavier components has a very large economic benefit.

Conventionally, the primary method of recovering the FCC fuel gas ethylene and ethane is through a cold box where the FCC absorber off-gas is cooled to very low temperatures of around −120° C. and then light ends are separated out through a series of distillation columns. However, the cold boxes are capitally intensive. Further, the cold boxes also face the problem of potential explosions from trace NO in the FCC fuel gas. NO in the FCC absorber off-gas condenses within the cold box, followed by subsequent reaction with oxygen to form heavier $NO_X$ compounds that subsequently react with dienes to form gums, which may explode when the cold box is warmed up. This condensation of NO is caused by the extremely low temperatures found in a cold box in the range of −100° C. to −120° C. This safety problem discourages companies from mixing FCC fuel gas within existing product recovery systems even when there is extra capacity in these recovery section.

U.S. Pat. No. 5,245,099 describes pressure swing adsorption (PSA) recovery of ethylene from FCC fuel gas. However, since the PSA cannot totally purify the ethylene and substantial methane (around 15%) is still present, this stream would require further purification at the ethylene cracker demethanizer column if it was sent as is. The ethylene cracker demethanizer column runs very cold (−100° C.) and is integrated with the cold box. This would mean that small amounts of NO present in the feed would get very cold and condense out and still end up in the cold box with the possibility of explosive $NO_X$ gum formation if PSA recovery of ethylene from FCC Fuel gas was practiced as described in U.S. Pat. No. 5,245,099.

Accordingly, it is desirable to provide apparatuses and processes for recovery of ethylene from FCC absorber off-gas in a safer and a cost-effective manner. Furthermore, other desirable features and characteristics of the present subject matter will become apparent from the subsequent detailed description of the subject matter and the appended claims, taken in conjunction with the accompanying drawings and this background of the subject matter.

BRIEF SUMMARY

Various embodiments contemplated herein relate to processes and apparatuses for recovery of ethylene. The exemplary embodiments taught herein recover ethylene from FCC absorber off-gas.

In accordance with an exemplary embodiment, a process is provided for the concentration and recovery of a heavy cut comprising ethylene, ethane and heavier hydrocarbons from a hydrocarbon feed stream comprising a light cut and the heavy cut, the light cut comprising hydrogen, nitrogen and methane. The process includes passing the hydrocarbon feed stream to an adsorption zone containing an adsorbent selective for the adsorption of the light cut, the adsorption zone adsorbing at least a portion of the light cut and recovering an adsorption zone effluent stream comprising the heavy cut. The adsorption zone effluent is passed to a demethanizer column to provide an overhead stream comprising hydrogen, nitrogen, methane, ethylene and ethane and a net bottoms stream comprising ethylene, ethane and the heavier hydrocarbons.

In accordance with another exemplary embodiment, a process is provided for the concentration and recovery of a heavy cut comprising ethylene, ethane and heavier components from a hydrocarbon feed stream comprising a light cut and the heavy cut, the light cut comprising hydrogen, nitrogen and methane. The process includes passing the hydrocarbon feed stream to an adsorption zone containing an adsorbent selective for the adsorption of the light cut, the adsorption zone adsorbing at least a portion of the light cut and recovering an adsorption zone effluent stream comprising the heavy cut. The adsorption zone effluent stream is compressed to provide a compressed adsorption zone effluent stream. The compressed adsorption zone effluent stream is cooled to provide a cooled adsorption zone effluent stream. The cooled adsorption zone effluent is passed to a demethanizer column to provide an overhead stream comprising hydrogen, nitrogen, methane, ethylene and ethane and a net bottoms stream comprising ethylene, ethane and the heavier hydrocarbons. Further, the overhead stream is recycled to the adsorption zone.

In accordance with yet another exemplary embodiment, an apparatus is provided for the concentration and recovery of a heavy cut comprising ethylene, ethane and heavier hydrocarbons from a hydrocarbon feed stream comprising a light cut and the heavy cut, the light cut comprising hydrogen, nitrogen and methane. The apparatus includes an adsorption zone comprising an adsorbent selective for the adsorption of the light cut, the adsorption zone configured to adsorb at least a portion of the light cut and recover an adsorption zone effluent stream comprising the heavy cut. A compressor is in fluid communication with the adsorption zone and is configured to compress the adsorption zone effluent stream to provide a compressed adsorption zone effluent stream. A cooling zone is in fluid communication with the compressor and configured to cool the compressed adsorption zone effluent stream to provide a cooled adsorption zone effluent stream. A demethanizer column is in fluid communication with the cooling zone and is configured to separate an overhead stream comprising, hydrogen, nitrogen, methane, ethylene and ethane from the cooled adsorption zone effluent stream to provide a net bottoms stream comprising ethylene, ethane and the heavier hydrocarbons. A recycle line extends from top of the demethanizer column to the adsorption zone for recycling the overhead stream to the adsorption zone.

BRIEF DESCRIPTION OF THE DRAWINGS

The various embodiments will hereinafter be described in conjunction with the following FIGURES, wherein like numerals denote like elements.

DEFINITIONS

As used herein, the term "stream" can include various hydrocarbon molecules and other substances.

The notation "$C_x$" means hydrocarbon molecules that have "x" number of carbon atoms, $C_x^+$ means hydrocarbon molecules that have "x" and/or more than "x" number of carbon atoms, and $C_x^-$ means hydrocarbon molecules that have "x" and/or less than "x" number of carbon atoms.

As used herein, the term "zone" can refer to an area including one or more equipment items and/or one or more sub-zones. Equipment items can include one or more reactors or reactor vessels, heaters, exchangers, pipes, pumps, compressors, controllers and columns. Additionally, an equipment item, such as a reactor, dryer, or vessel, can further include one or more zones or sub-zones.

As used herein, the term "overhead stream" can mean a stream withdrawn at or near a top of a vessel, such as a column.

As used herein, the term "bottom stream" can mean a stream withdrawn at or near a bottom of a vessel, such as a column.

As depicted, process flow lines in the FIGURES can be referred to interchangeably as, e.g., lines, pipes, feeds, gases, products, discharges, parts, portions, or streams.

The term "communication" means that material flow is operatively permitted between enumerated components.

The term "downstream communication" means that at least a portion of material flowing to the subject in downstream communication may operatively flow from the object with which it communicates.

The term "upstream communication" means that at least a portion of the material flowing from the subject in upstream communication may operatively flow to the object with which it communicates.

The term "column" means a distillation column or columns for separating one or more components of different volatilities.

The term "predominant" means a majority, suitably at least 80 wt % and preferably at least 90 wt %.

DETAILED DESCRIPTION

The following detailed description is merely exemplary in nature and is not intended to limit the various embodiments or the application and uses thereof. Furthermore, there is no intention to be bound by any theory presented in the preceding background or the following detailed description.

Figure 1:
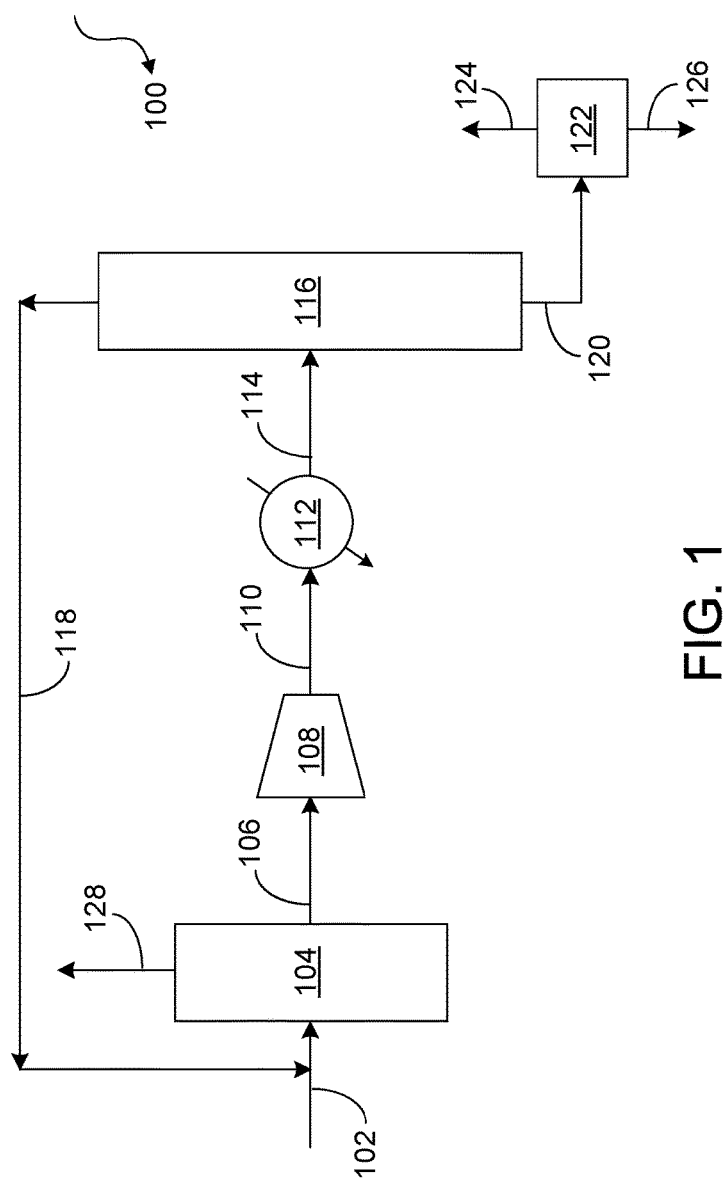
FIG. 1 is a schematic diagram of a process and an apparatus for recovery of ethylene in accordance with an exemplary embodiment.

An embodiment of a process for recovery of ethylene is addressed with reference to a process and apparatus 100 for recovery of ethylene from FCC absorber off gas as shown in FIG. 1. The apparatus and method 100 includes an adsorption zone 104, a compressor 108, a cooler 112, a demethanizer column 116 and a $C_2$ splitter 122. For the purpose of the explanation of the instant embodiment, the adsorption zone 104 is a pressure swing adsorption zone 104.

In accordance with the process and as shown in FIG. 1, a first hydrocarbon feed 102 is provided to the pressure swing adsorption zone 104. The first hydrocarbon feed 102 includes a heavy cut and a light cut. The heavy cut may include hydrocarbons such as ethylene, ethane, propane, propylene and other heavier hydrocarbons. The light cut may include methane and lighter gases such as hydrogen and nitrogen. Exemplary compositions of the FCC absorber off-gas which can be the hydrocarbon feed 102 of the present invention are shown in Table 1 below.

TABLE 1

FCC fuel gas composition data for two FCC streams

| | | Stream # | |
| --- | --- | --- | --- |
| | | 25 | 31 |
| | Description | FCCU1 (Total) | FCCU3 |
| Component | LHV | mol % | mol % |
| Hydrogen | 274 | 12.35 | 28.88 |
| Methane | 909 | 34.46 | 31.04 |
| Ethane | 1619 | 14.48 | 12.71 |
| Ethylene | 1499 | 13.95 | 13.96 |
| Propane | 2315 | 1.34 | 0.52 |
| Propylene | 2162 | 4.25 | 1.93 |
| Iso-Butane | 3011 | 1.35 | 0.25 |
| n-Butane | 3011 | 0.31 | 0.06 |
| 1-Butene | 2876 | 0.46 | 0.09 |
| Iso-Butene | 2876 | 0.47 | 0.11 |
| Trans-Butene | 2876 | 0.43 | 0.09 |
| Cis-Butene | 2876 | 0.29 | 0.06 |
| Butadiene | 2876 | 0 | 0 |
| iso-Pentane | 3704 | 0.4 | 0.07 |
| n-Pentane | 3704 | 0.03 | 0 |
| C6+ | 4404 | 0.08 | 0.06 |
| Nitrogen | 0 | 11.2 | 6.51 |
| Carbon Dioxide | 0 | 2.91 | 1.8 |
| Carbon Monoxide | 321 | 0.62 | 0.64 |
| Hydrogen Sulfide | — | 0.63 | 1.2 |
| Pressure, kPa (psig) | — | 1793 (260) | 1793 (260) |

A number of unit operations (not shown) may be performed on the hydrocarbon feed 102 prior to passing through the pressure swing adsorption zone 104 to remove undesirable impurities. The unit operations may include, but are not limited to: passing the hydrocarbon feed 102 through at least one of an amine absorber unit, a drier, an acetylene converter and one or more treaters.

Referring back to FIG. 1, the pressure swing adsorption zone 104 includes an adsorbent selective for the adsorption of the light cut. Examples of an adsorbent selective for the adsorption of the light cut include, but are not limited to, a silica gel adsorbent. The pressure swing adsorption zone 104 adsorbs at least a portion of hydrogen, nitrogen and methane present in the light cut. In an exemplary embodiment, at least about 80 wt % of nitrogen and hydrogen present in the light cut is adsorbed. Further, at least about 70 wt % of methane present in the light cut is adsorbed in the pressure swing adsorption zone 104. In another exemplary embodiment, at least about 75 wt % of methane present in the light cut is adsorbed in the pressure swing adsorption zone 104. The portion of the light cut being adsorbed in the pressure swing adsorption zone 104 may be rejected as light ends 128.

An adsorption zone effluent stream 106 including the heavy cut is withdrawn from the pressure swing adsorption zone 104. The adsorption zone effluent stream 106 may further include the remaining amount of the light cut not adsorbed by the pressure swing adsorption zone 104. The adsorption zone effluent stream 106 may have a pressure in the range of about 0.2 to about 2.1 bar (g). The adsorption zone effluent stream 106 is compressed in the compressor 108 to provide a compressed adsorption zone effluent stream 110. In accordance with an embodiment, the compressor 108 may be a two-stage compressor. In one example, the compressed adsorption zone effluent stream 110 may have a pressure of at least about 28 bar (g). In another example, the compressed adsorption zone effluent stream 110 may have a pressure of at least about 50 bar (g). The compressed adsorption zone effluent stream 110 is passed to the cooler 112 for cooling the compressed adsorption zone effluent stream 110. In an exemplary embodiment, the compressed adsorption zone effluent stream 110 is cooled to a temperature of at least about −22° F. (−30° C.) in the cooler 112. In another exemplary embodiment, the compressed adsorption zone effluent stream 110 is cooled to a temperature of at least about −4° F. (−20° C.) in the cooler 112.

A cooled adsorption zone effluent stream 114 is withdrawn from the cooler 112 and passed to the demethanizer column 116. In the demethanizer column 116, the $C_2^-$ hydrocarbon product is fractionated, such as by conventional distillation, to provide an overhead stream 118 and a demethanized net bottoms stream 120. The overhead stream 118 includes ethylene, ethane and a remaining amount of methane, hydrogen and nitrogen that is not absorbed by the pressure swing adsorption zone 104. The overhead stream 118 is recycled to an inlet of the pressure swing adsorption zone 104. In various embodiments, the overhead stream 118 may pass through the cooler 112 prior to being recycled to the inlet of the pressure swing adsorption zone 104. The demethanizer column 116 operates at significantly warmer temperatures of at least about −40° F. (−40° C.) in contrast to conventional teachings. In one example, the demethanizer column 116 operates at a temperature of at least −49° F. (−45° C.) temperature. According to the present invention, it was unexpectedly discovered that for the overhead stream 118, the demethanizer column 116 can be operated at a demethanizing temperature of greater than about −40° F. (−40° C.), rather than the traditional cryogenic demethanizer column temperature of about −140° F. (−95° C.). Thus, the overall ethylene separation objectives can be met without using an ethylene refrigerant system, without a significant loss of ethylene product, without significant increases in ethylene recycle, and without considerable increases in operating cost and capital cost. This permits the demethanizer column zone to be cooled with a propylene refrigerant (less than −49° C.) rather than an ethylene refrigerant-based cooling system (less than −100° C.) for recovering ethylene. Further, the capital cost of the cold box system is less than half of the cold box system in a traditional fractionation system design. Since traditional fractionation systems often use turbo-expanders to reach very cold temperatures, the proposed system avoids such costly and often unreliable equipment. Moreover, there is no safety issue as the instant process can separate trace NO out, which is a safety hazard for cold box.

Turning back to FIG. 1, the net bottoms stream 120 is withdrawn from the bottom of the demethanizer column 116. The net bottoms stream 120 includes ethylene, ethane and the heavier hydrocarbons. In an embodiment, the net bottoms stream 120 includes less than about 1 wt % of the light cut present in the hydrocarbon feed stream 102. In another embodiment, the net bottoms stream 120 includes less than about 0.03 wt % of the light cut present in the hydrocarbon feed stream 102. The net bottoms stream 120 predominantly includes ethylene and ethane. In accordance with an exemplary embodiment, the net bottoms stream 120 includes at least about 85 wt % of ethylene present in the hydrocarbon feed stream 102. In accordance with another exemplary embodiment, the net bottoms stream 120 includes at least about 90 wt % of ethylene present in the hydrocarbon feed stream 102.

The $C_2$ splitter 122 is in downstream communication with the demethanizer column 116 and is configured to recover ethylene from the net bottoms streams 120. In an exemplary embodiment, a deethanizer column (not shown) may also be present between the demethanizer column 116 and the $C_2$ splitter 122. In such a scenario, the net bottoms stream 120 is fractionated, such as by conventional distillation, to separate a deethanizer overhead stream comprising predominantly ethane and ethylene from a deethanized $C_3^+$ bottoms stream (which may be removed from the system) and subsequently sending the deethanizer overhead stream to the $C_2$ splitter. The net bottoms streams 120 is sent to the $C_2$ splitter 122 to recover a high purity ethylene product stream (greater than 99.5 mol %). The $C_2$ splitter 122 produces an overhead stream 124 including high purity ethylene stream and an ethane rich bottoms stream 126. The ethane rich bottoms stream 126, can be flashed and used to cool demethanizer feed, or a portion thereof can advantageously be recycled to the demethanizer column 116, or can alternatively be used as fuel. If the ethane is recycled back to the demethanizer column 116, the demethanizer column 116 can be changed from a refluxed and reboiled distillation column to a reboiled absorber and can be used to absorb ethylene and heavier material in the demethanizer, thus avoiding the need for a condenser and propylene refrigerant. Conditions on the $C_2$ splitter 122 are determined as dictated by the state of the art for these separations. The $C_2$ splitter 122 can include one or more reboilers, one or more side condensers and can also include pumps, drums, control valves, and other typical processing equipment that are standard in the industry.

Figure 2:
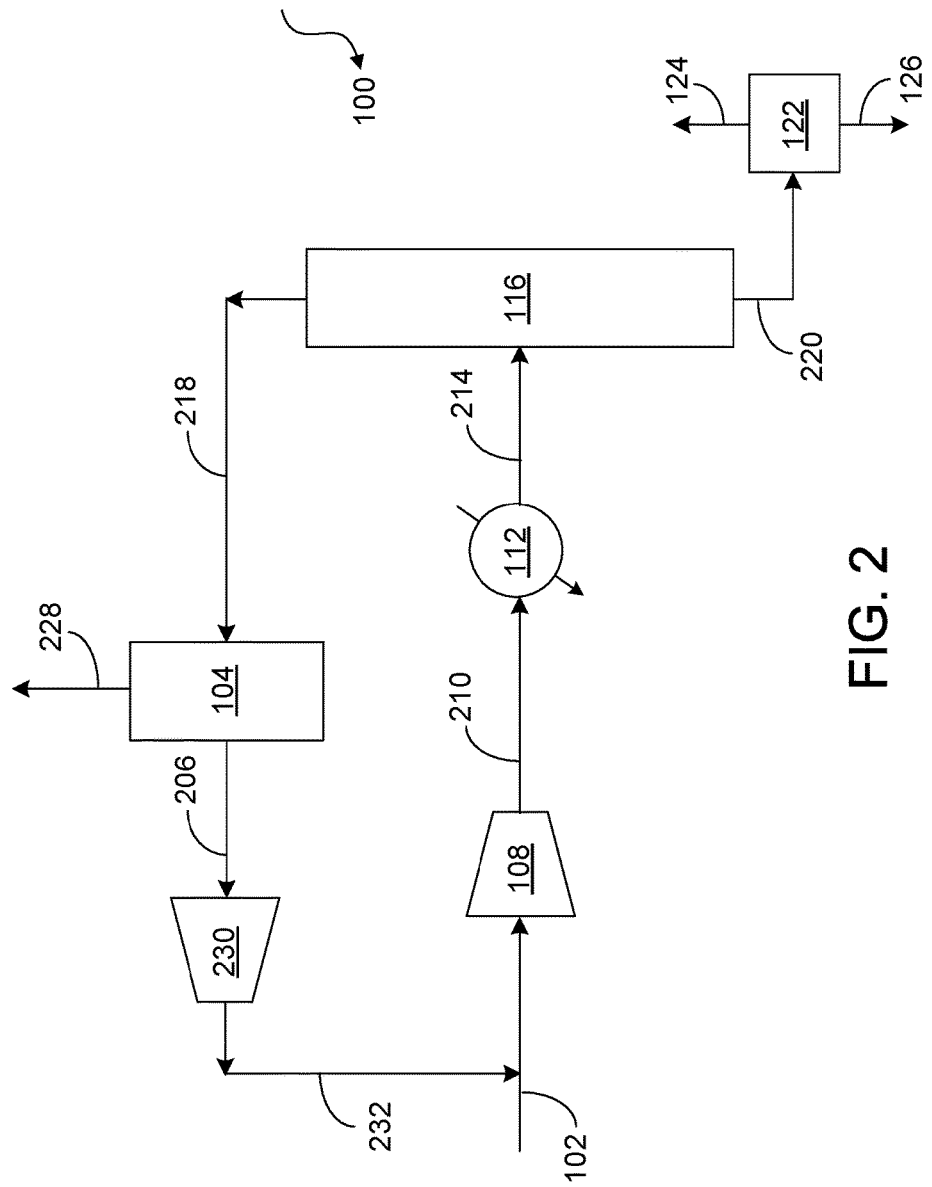
FIG. 2 is a schematic diagram of a process and an apparatus for recovery of ethylene in accordance with another exemplary embodiment.

Referring to FIG. 2, another version of the exemplary apparatus 100 is depicted with the apparatus and method 100 includes the pressure swing adsorption zone 104, an intermediate compressor 230, the compressor 108, the cooler 112, the demethanizer column 116 and the $C_2$ splitter 122 as described above. Many of the elements in FIG. 2 have the same configuration as in FIG. 1 and bear the same respective reference number and have similar operating conditions. Further, the temperature and pressure of various streams are similar to the corresponding streams in FIG. 1, unless specified otherwise. The hydrocarbon feed 102 passes through the compressor 108 to provide a compressed adsorption zone effluent stream 210. The compressed adsorption zone effluent stream 210 is passed to the cooler 112 for cooling.

A cooled adsorption zone effluent stream 214 is withdrawn from the cooler 112 and passed to the demethanizer column 116. The demethanizer column 116 provides an overhead stream 218 and a net bottoms stream 220. The overhead stream 218 includes ethylene, ethane, methane, hydrogen and nitrogen. The net bottoms stream 220 includes ethylene, ethane and heavier hydrocarbons. The overhead stream 218 is sent to the pressure swing adsorption zone 104. The pressure swing adsorption zone 104 includes an adsorbent selective for the adsorption of the light cut. The pressure swing adsorption zone 104 adsorbs at least a portion of hydrogen, nitrogen and methane present in the light cut of the overhead stream 218. The portion of the light cut being adsorbed in the pressure swing adsorption zone 104 may be rejected as light ends 228. In an exemplary embodiment, at least about 80 wt % of nitrogen and hydrogen present in the overhead stream 218 is adsorbed. Further, at least about 70 wt % of methane present in the overhead stream 218 is adsorbed in the pressure swing adsorption zone 104. In another exemplary embodiment, at least about 75 wt % of methane present in the light cut is adsorbed in the pressure swing adsorption zone 104. An adsorption zone effluent stream 206 including predominantly the heavy cut is withdrawn from the pressure swing adsorption zone 104 and subsequently passed through the intermediate compressor 230. A compressed stream 232 is obtained from the intermediate compressor 230 and subsequently passed to the compressor 108, the cooler 112, the demethanizer column 116 and $C_2$ splitter 122 in accordance with the process steps as discussed in detail with respect to FIG. 1.

EXAMPLE

The following is an example of the ethylene recovery using a combination of pressure swing adsorption and demethanizer column, in accordance with an exemplary embodiment, that is similarly configured to the apparatus and method 100 illustrated in FIG. 1. The example is provided for illustration purposes only and is not meant to limit the various embodiments of apparatuses and methods for naphtha hydrotreating in any way.

In an exemplary case study, the instant process was applied to a FCC unit. Based on the average FCC Units absorber off-gas availability of 2000 Mscfh (57,000 m$^3$/hr) at 275 psig (1896 kPa) delivery pressure from the FCCU Vapor Recovery Units, +/−50% erected Gulf Coast cost estimate was conducted for this recovery scheme. The total estimated installed cost was approximately 27 MM$. The individual approximate cost contributions for major equipment are shown in Table 2 below. The estimated capital cost was approximately one-quarter of the cost of a new cold box.

TABLE 2

Major Equipment Costs for UOP PSA + Warm
Demethanizer column Ethylene Recovery Unit

|  | Capital Cost in MM$ installed |
|---|---|
| Pressure Swing Adsorption | 8.9 |
| Compression | 7.1 |
| Refrigeration | 5 |
| Distillation | 1.7 |
| Other | 3.8 |

Further, the estimated utilities were:
3.0 MW for refrigeration
3.9 MW for compression
0.15 MW for pumps
15 MMBtu/h for cooling water Based on 0.05$/kW-h and 8000 operating hours per year, the estimated total utilities cost was approximately 2.9 MM$/year. In summary, the overall benefit was approximately 30 MM$/year. The payout is less than 1 year.

Specific Embodiments

While the following is described in conjunction with specific embodiments, it will be understood that this description is intended to illustrate and not limit the scope of the preceding description and the appended claims.

A first embodiment of the invention is a process for the concentration and recovery of a heavy cut comprising ethylene, ethane and heavier hydrocarbons from a hydrocarbon feed stream comprising a light cut and the heavy cut, the light cut comprising hydrogen, nitrogen and methane, the process comprising the following steps: a) passing the hydrocarbon feed stream to an adsorption zone containing an adsorbent selective for the adsorption of the light cut, the adsorption zone adsorbing at least a portion of the light cut and recovering an adsorption zone effluent stream comprising the heavy cut; and b) passing the adsorption zone effluent to a demethanizer column to provide an overhead stream comprising hydrogen, nitrogen, methane, ethylene and ethane and a net bottoms stream comprising ethylene, ethane and the heavier hydrocarbons. An embodiment of the invention is one, any or all of prior embodiments in this paragraph up through the first embodiment in this paragraph further comprising recycling the overhead stream to the adsorption zone. An embodiment of the invention is one, any or all of prior embodiments in this paragraph up through the first embodiment in this paragraph further comprising sending the net bottoms stream to a $C_2$ splitter for recovery of ethylene. An embodiment of the invention is one, any or all of prior embodiments in this paragraph up through the first embodiment in this paragraph, wherein the adsorption zone adsorbs at least about 70% of methane present in the light cut. An embodiment of the invention is one, any or all of prior embodiments in this paragraph up through the first embodiment in this paragraph, wherein the adsorption zone adsorbs at least about 80% of each of hydrogen and nitrogen present in the light cut. An embodiment of the invention is one, any or all of prior embodiments in this paragraph up through the first embodiment in this paragraph, wherein the demethanizer column operates at a demethanizing temperature at least about −49° F. (−45° C.). An embodiment of the invention is one, any or all of prior embodiments in this paragraph up through the first embodiment in this paragraph, wherein the adsorption zone effluent stream is compressed prior to being passed to the demethanizer column. An embodiment of the invention is one, any or all of prior embodiments in this paragraph up through the first embodiment in this paragraph, wherein the adsorption zone effluent stream is compressed to a pressure of at least about 28 bar (g). An embodiment of the invention is one, any or all of prior embodiments in this paragraph up through the first embodiment in this paragraph, wherein the adsorption zone effluent stream is cooled subsequent to the compression and prior to being passed to the demethanizer column. An embodiment of the invention is one, any or all of prior embodiments in this paragraph up through the first embodiment in this paragraph, wherein the adsorption zone effluent stream is cooled to a temperature of at least about −22° F. (−30° C.). An embodiment of the invention is one, any or all of prior embodiments in this paragraph up through the first embodiment in this paragraph, wherein the net bottoms stream comprises less than about 1 wt % of the light cut present in the hydrocarbon feed stream. An embodiment of the invention is one, any or all of prior embodiments in this paragraph up through the first embodiment in this paragraph, wherein the net bottoms stream comprises at least about 85 wt % of ethylene present in the hydrocarbon feed stream. An embodiment of the invention is one, any or all of prior embodiments in this paragraph up through the first embodiment in this paragraph, wherein the adsorbent selective for the adsorption of the light cut comprises a silica gel adsorbent.

A second embodiment of the invention is a process for the concentration and recovery of a heavy cut comprising ethylene, ethane and heavier hydrocarbons from a hydrocarbon feed stream comprising a light cut and the heavy cut, the light cut comprising hydrogen, nitrogen and methane, the process comprising the following steps a) passing the hydrocarbon feed stream to an adsorption zone containing an adsorbent selective for the adsorption of the light cut, the adsorption zone adsorbing at least a portion of the light cut and recovering an adsorption zone effluent stream comprising the heavy cut; b) compressing the adsorption zone effluent stream to provide a compressed adsorption zone effluent stream; c) cooling the compressed adsorption zone effluent stream to provide a cooled adsorption zone effluent stream; d) passing the cooled adsorption zone effluent to a demethanizer column to provide an overhead stream comprising hydrogen, nitrogen, methane, ethylene and ethane and a net bottoms stream comprising ethylene, ethane and the heavier hydrocarbons; and e) recycling the overhead stream to the adsorption zone. An embodiment of the invention is one, any or all of prior embodiments in this paragraph up through the second embodiment in this paragraph further comprising sending the net bottoms stream to a $C_2$ splitter for recovery of ethylene. An embodiment of the invention is one, any or all of prior embodiments in this paragraph up through the second embodiment in this paragraph, wherein the demethanizer column operates at a demethanizing temperature at least about −49° F. (−45° C.). An embodiment of the invention is one, any or all of prior embodiments in this paragraph up through the second embodiment in this paragraph, wherein the net bottoms stream comprises less than about 1 wt % of the light cut present in the hydrocarbon feed stream. An embodiment of the invention is one, any or all of prior embodiments in this paragraph up through the second embodiment in this paragraph, wherein the net bottoms stream comprises at least about 85 wt % of ethylene present in the hydrocarbon feed stream.

A third embodiment of the invention is an apparatus for the concentration and recovery of a heavy cut comprising ethylene, ethane and heavier hydrocarbons from a hydrocarbon feed stream comprising a light cut and the heavy cut, the light cut comprising hydrogen, nitrogen and methane, the apparatus comprising a) an adsorption zone comprising an adsorbent selective for the adsorption of the light cut, the adsorption zone configured to adsorb at least a portion of the light cut and recover an adsorption zone effluent stream comprising the heavy cut; b) a compressor in fluid communication with the adsorption zone and configured to compress the adsorption zone effluent stream to provide a compressed adsorption zone effluent stream; c) a cooling zone in fluid communication with the compressor and configured to cool the compressed adsorption zone effluent stream to provide a cooled adsorption zone effluent stream; d) a demethanizer column in fluid communication with the cooling zone and configured to separate an overhead stream comprising, hydrogen, nitrogen, methane, ethylene and ethane from the cooled adsorption zone effluent stream to provide a net bottoms stream comprising ethylene, ethane and the heavier hydrocarbons; and e) a recycle line extending from top of the demethanizer column to the adsorption zone for recycling the overhead stream to the adsorption zone. An embodiment of the invention is one, any or all of prior embodiments in this paragraph up through the third embodiment in this paragraph further comprising a $C_2$ splitter in fluid communication with the demethanizer column configured to recover ethylene from the net bottoms streams.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

The invention claimed is:

1. A process for the concentration and recovery of a heavy cut comprising ethylene, ethane and heavier hydrocarbons from a FCC absorber off-gas stream comprising a light cut and the heavy cut, the light cut comprising hydrogen, nitrogen and methane, the process comprising the following steps:
   a) passing the hydrocarbon feed stream to an adsorption zone containing a silica gel adsorbent selective for the adsorption of at least about 80 wt. % each of nitrogen and hydrogen and at least about 70 wt. % of methane present in the light cut, and recovering an adsorption zone effluent stream comprising the heavy cut;
   b) passing the adsorption zone effluent to a demethanizer column operated at a demethanizing temperature at least about −49° F. to provide an overhead stream comprising hydrogen, nitrogen, methane, ethylene and ethane and a net bottoms stream comprising ethylene, ethane and the heavier hydrocarbons; and
   c) recycling the overhead stream to the adsorption zone.

2. The process of claim 1 further comprising sending the net bottoms stream to a $C_2$ splitter for recovery of ethylene.

3. The process of claim 1, wherein the adsorption zone effluent stream is compressed prior to being passed to the demethanizer column.

4. The process of claim 3, wherein the adsorption zone effluent stream is compressed to a pressure of at least about 28 bar (g).

5. The process of claim 3, wherein the adsorption zone effluent stream is cooled subsequent to the compression and prior to being passed to the demethanizer column.

6. The process of claim 5, wherein the adsorption zone effluent stream is cooled to a temperature of at least about −22° F. (−30° C.).

7. The process of claim 1, wherein the net bottoms stream comprises less than about 1 wt % of the light cut present in the hydrocarbon feed stream.

8. The process of claim 1, wherein the net bottoms stream comprises at least about 85 wt % of ethylene present in the hydrocarbon feed stream.

9. A process for the concentration and recovery of a heavy cut comprising ethylene, ethane and heavier hydrocarbons from a FCC absorber off-gas stream comprising a light cut and the heavy cut, the light cut comprising hydrogen, nitrogen and methane, the process comprising the following steps:
   a) passing the hydrocarbon feed stream to an adsorption zone containing a silica gel adsorbent selective for the adsorption of at least about 80 wt. % each of nitrogen and hydrogen and at least about 70 wt. % of methane present in the light cut, and recovering an adsorption zone effluent stream comprising the heavy cut;

b) compressing the adsorption zone effluent stream to provide a compressed adsorption zone effluent stream;

c) cooling the compressed adsorption zone effluent stream to provide a cooled adsorption zone effluent stream;

d) passing the cooled adsorption zone effluent to a demethanizer column to provide an overhead stream comprising hydrogen, nitrogen, methane, ethylene and ethane and a net bottoms stream comprising ethylene, ethane and the heavier hydrocarbons; and e) recycling the overhead stream to the adsorption zone.

10. The process of claim 9 further comprising sending the net bottoms stream to a $C_2$ splitter for recovery of ethylene.

11. The process of claim 9, wherein the demethanizer column operates at a demethanizing temperature at least about −49° F. (−45° C.).

12. The process of claim 9, wherein the net bottoms stream comprises less than about 1 wt % of the light cut present in the hydrocarbon feed stream.

13. The process of claim 9, wherein the net bottoms stream comprises at least about 85 wt % of ethylene present in the hydrocarbon feed stream.

\* \* \* \* \*